United States Patent
Tefferi

(10) Patent No.: US 11,123,359 B2
(45) Date of Patent: Sep. 21, 2021

(54) METHODS AND MATERIALS FOR TREATING HEMATOLOGICAL MALIGNANCIES

(71) Applicant: Mayo Foundation for Medical Education and Research, Rochester, MN (US)

(72) Inventor: Ayalew Tefferi, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 177 days.

(21) Appl. No.: 15/034,822

(22) PCT Filed: Nov. 5, 2014

(86) PCT No.: PCT/US2014/064112
§ 371 (c)(1),
(2) Date: May 5, 2016

(87) PCT Pub. No.: WO2015/069758
PCT Pub. Date: May 14, 2015

(65) Prior Publication Data
US 2016/0287625 A1    Oct. 6, 2016

Related U.S. Application Data

(60) Provisional application No. 61/904,195, filed on Nov. 14, 2013, provisional application No. 61/900,854, filed on Nov. 6, 2013.

(51) Int. Cl.
| | | |
|---|---|---|
| *C12Q 1/6883* | (2018.01) | |
| *C12Q 1/6886* | (2018.01) | |
| *A61K 31/7125* | (2006.01) | |
| *A61K 47/54* | (2017.01) | |

(52) U.S. Cl.
CPC ........ *A61K 31/7125* (2013.01); *A61K 47/543* (2017.08); *C12Q 1/6883* (2013.01); *C12Q 1/6886* (2013.01); *C12Q 2600/106* (2013.01); *C12Q 2600/156* (2013.01); *G01N 2800/22* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 7,989,428 B2 | 8/2011 | Go et al. | |
| 2013/0216742 A1* | 8/2013 | DeMartino | A61J 1/00 428/34.4 |
| 2013/0316014 A1* | 11/2013 | Maciejewski | C12Q 1/6886 424/577 |
| 2014/0163090 A1* | 6/2014 | Stuart | A61K 49/0423 514/44 R |
| 2020/0063214 A1 | 2/2020 | Bussolari et al. | |

FOREIGN PATENT DOCUMENTS

| | | |
|---|---|---|
| WO | WO2011098901 | 8/2011 |
| WO | WO2013059738 | 4/2013 |
| WO | WO2014088785 | 6/2014 |

OTHER PUBLICATIONS

Mummidi et al (Journal of Biological Chemistry 2000 vol. 275 No. 25 pp. 18946-18961) (Year: 2000).*
Lasho et al. ( Leukemia vol. 26 Nov. 2011 p. 1135) (Year: 2011).*
Lasho et al. (Blood Nov. 16, 2012, vol. 120 p. 430 ) (Year: 2012).*
Asai et al., "A novel telomerase template antagonist (GRN163) as a potential anticancer agent," *Cancer Res.*, 63(14):3931-3939, Jul. 15, 2003.
Cazzola and Invernizzi, "Ring sideroblasts and sideroblastic anemias," *Haematologica*, 96(6):789-792, Jun. 2011.
ClinicalTrials.gov, Identifier: NCT01731951, "Imetelstat Sodium in Treating Patients With Primary or Secondary Myelofibrosis," Nov. 18, 2012, 4 pages.
Furney et al., "SF3B1 mutations are associated with alternative splicing in uveal melanoma," *Cancer Discov.*, 3(10):1122-1129. Epub Jul. 16, 2013.
Geron 2012 Annual Report: Letter to Stockholders Proxy, Aug. 4, 2013. Article retrieved from the Internet:<http://phx.corporate-ir.net/External.Fileitem=UGFyZW50SUQ9NTAyMjg5fENoaWxkSUQ9NTQyODA4fFR5cGU9MQ==&t=1> on Feb. 20, 2015, 121 pages.
Graubert et al., "Recurrent mutations in the U2AF1 splicing factor in myelodysplastic syndromes," *Nat Genet.*, 44(1):53-57, Dec. 11, 2011.
Gryaznov, "Oligonucleotide n3'-->p5' phosphoramidates and thio-phoshoramidates as potential therapeutic agents," *Chem Biodivers.*, 7(3):477-493, Mar. 2010.
Herbert et al., "Lipid modification of GRN163, an N3'-->P5' thio-phosphoramidate oligonucleotide, enhances the potency of telomerase inhibition," *Oncogene*, 24(33):5262-5268, Aug. 4, 2005.
Lasho et al., "SRSF2 mutations in primary myelofibrosis: significant clustering with IDH mutations and independent association with inferior overall and leukemia-free survival," *Blood*, 120(20):4168-4171, Epub Sep. 11, 2012.
Makishima et al., Mutations in the spliceosome machinery, a novel and ubiquitous pathway in leukemogenesis, *Blood*, 119(14):3203-3210, Epub Feb. 9, 2012.
Meggendorfer et al., "SRSF2 mutations in 275 cases with chronic myelomonocytic leukemia (CMML)," *Blood*, 120(15):3080-3088, Epub Aug. 23, 2012.

(Continued)

*Primary Examiner* — Katherine D Salmon
(74) *Attorney, Agent, or Firm* — Fish & Richardson P.C.

(57) ABSTRACT

This document provides methods and materials involved in treating hematological malignancies. For example, methods and materials for using telomerase inhibitors to treat hematological malignancies such as hematological malignancies with a spliceosome mutation genotype or presenting with ringed sideroblasts within bone marrow are provided.

7 Claims, No Drawings
Specification includes a Sequence Listing.

(56) References Cited

OTHER PUBLICATIONS

Papemmanuil et al., "Somatic SF3B1 mutation in myelodysplasia with ring sideroblasts," *N Engl J Med.*, Oct. 13, 2011;365(15):1384-1395, Epub Sep. 26, 2011.

Przychodzen et al., "Patterns of missplicing due to somatic U2AF1 mutations in myeloid neoplasms," *Blood*, 122(6):999-1006, Epub Jun. 17, 2013.

Puri et al., "Novel therapeutics targeting telomerase and telomeres," *Journal of Cancer Science & Therapy*, Sep. 23, 2013, vol. 5, pp. 1-3.

Thol et al., "Prognostic significance of ASXL1 mutations in patients with myelodysplastic syndromes," *J Clin Oncol.*, 29(18):2499-506, Epub May 16, 2011.

International Search Report and Written Opinion for PCT/US2014/064112, dated Mar. 18, 2015, 5 pages.

International Preliminary Report on Patentability for PCT/US2014/064112, dated May 10, 2016, 8 pages.

Extended European Search Report in International Application No. 14860231.1, dated Jun. 16, 2017, 5 pages.

Tefferi et al., "Imetelstat therapy in refractory anemia with ring sideroblasts with or without thrombocytosi," *Blood.*, 6(3):e405, Mar. 11, 2016, 2 pages.

Tefferi et al., "Imetelstat, a Telomerase Inhibitor, Induces Morphologic and Molecular Remissions in Myelofibrosis and Reversal Of Bone Marrow Fibrosis," *Blood.*, Dec. 1, 2013, Retrieved from the Internet: URL: http://www.bloodjournal.org/content/122/21/662 Retrieved on May 26, 2017, 5 pages.

Mascarenhas et al., "Imetelstat Is Effective Treatment for Patients with Intermediate-2 or High-Risk Myelofibrosis Who Have Relapsed on or Are Refractory to Janus Kinase Inhibitor Therapy: Results of a Phase 2 Randomized Study of Two Dose Levels," Blood, 132(Supplement 1):685, 2018.

Mascarenhas, "[PowerPoint] Imetelstat is effective treatment for patients with intermediate-2 or high-risk myelofibrosis who have relapsed on or are refractory to Janus kinase inhibitor therapy: results of a phase 2 randomized study of two dose levels," Presented at ASH, Dec. 3, 2018.

\* cited by examiner

METHODS AND MATERIALS FOR TREATING HEMATOLOGICAL MALIGNANCIES

CROSS REFERENCE TO RELATED APPLICATIONS

This application is a National Stage application under 35 U.S.C. § 371 of International Application No. PCT/US2014/064112, having an International Filing Date of Nov. 5, 2014, which claims the benefit of U.S. Provisional Application Ser. No. 61/900,854, filed Nov. 6, 2013 and U.S. Provisional Application Ser. No. 61/904,195, filed Nov. 14, 2013. The disclosure of the prior applications are considered part of (and are incorporated by reference in) the disclosure of this application.

BACKGROUND

1. Technical Field

This document relates to methods and materials involved in treating hematological malignancies. For example, this document provides methods and materials for using telomerase inhibitors to treat hematological malignancies such as hematological malignancies with a spliceosome mutation genotype or presenting with ringed sideroblasts within bone marrow.

2. Background Information

Hematological malignancies are cancers that affect blood, bone marrow, and/or lymph nodes. Myelofibrosis is a type of hematological malignancy (e.g., a chronic leukemia or bone marrow disorder) that disrupts the normal production of blood cells. The result can be scarring of bone marrow, leading to severe anemia, weakness, fatigue, and an enlarged spleen and liver. Refractory anemia with ringed sideroblasts (RARS) is another type of hematological malignancy. RARS typically has 5 percent or less myeloblasts in bone marrow. RARS can be distinguished from refractory anemia based on having erythroid cells with abnormal ringed sideroblasts (e.g., about 15 percent of erythroid cells with abnormal ringed sideroblasts).

SUMMARY

This document provides methods and materials related to treating hematological malignancies. For example, this document provides methods and materials for using a telomerase inhibitor (e.g., Imetelstat (GRN163) or Imetelstat sodium (GRN163L)) to treat a hematological malignancy. In some cases, a telomerase inhibitor such as Imetelstat or Imetelstat sodium can be used to treat hematological malignancies with a spliceosome mutation genotype or presenting with ringed sideroblasts within bone marrow. For example, a telomerase inhibitor such as Imetelstat or Imetelstat sodium can be used to treat myelofibrosis (e.g., primary myelofibrosis or secondary myelofibrosis), myelofibrosis with a spliceosome mutation genotype, myelofibrosis presenting with ringed sideroblasts within bone marrow, or RARS.

As described herein, humans with a hematological malignancy can be assessed to determine the presence of a spliceosome mutation genotype, ringed sideroblasts within bone marrow, or both. If either or both are present, then that human can be treated with a telomerase inhibitor such as Imetelstat or Imetelstat sodium. In such cases, the dose of Imetelstat or Imetelstat sodium can be less than 9.4 mg/kg/month (e.g., the dose can be between 8.0 mg/kg/month and 6.0 mg/kg/month). Also, in such cases, even if the dose is 9.4 mg/kg/month or greater, the human can be instructed to undergo (or subjected to) increased monitoring for drug toxicity. For example, a human presenting with a hematological malignancy having the presence of a spliceosome mutation genotype, ringed sideroblasts within bone marrow, or both who is treated with a telomerase inhibitor such as Imetelstat or Imetelstat sodium can be monitored for myelosuppression (e.g., decreased or dangerously low platelet and/or white blood cell counts).

In general, one aspect of this document features a method for treating a hematological malignancy. The method comprises, or consists essentially of, administering imetelstat or imetelstat sodium to a mammal identified as having a hematological malignancy with the presence of a spliceosome mutation genotype, ringed sideroblasts within bone marrow, or both under conditions wherein the hematological malignancy is treated. The mammal can be a human. The method can comprise administering imetelstat sodium to the mammal. The hematological malignancy can be myelofibrosis. The hematological malignancy can be refractory anemia with ringed sideroblasts.

In another aspect, this document features a method for reversing bone marrow fibrosis in a mammal with myelofibrosis. The method comprises, or consists essentially of, administering imetelstat or imetelstat sodium to the mammal under conditions wherein the presence of the bone marrow fibrosis within the mammal is reduced. The mammal can be a human. The method can comprise administering imetelstat sodium to the mammal.

In another aspect, this document features a method for treating a hematological malignancy. The method comprises, or consists essentially of, (a) identifying a mammal as having a hematological malignancy with the presence of a spliceosome mutation genotype, ringed sideroblasts within bone marrow, or both, and (b) administering imetelstat or imetelstat sodium to the mammal under conditions wherein the hematological malignancy is treated. The mammal can be a human. The method can comprise administering imetelstat sodium to the mammal. The hematological malignancy can be myelofibrosis. The hematological malignancy can be refractory anemia with ringed sideroblasts.

In another aspect, this document features a method for treating a hematological malignancy. The method comprises, or consists essentially of, administering imetelstat or imetelstat sodium to a mammal identified as having a hematological malignancy with a wild-type or germline ASXL1 genotype under conditions wherein the hematological malignancy is treated. The mammal can be a human. The method can comprise administering imetelstat sodium to the mammal. The hematological malignancy can be myelofibrosis. The hematological malignancy can be refractory anemia with ringed sideroblasts.

In another aspect, this document features a method for treating a hematological malignancy. The method comprises, or consists essentially of, (a) identifying a mammal as having a hematological malignancy with a wild-type or germline ASXL1 genotype, and (b) administering imetelstat or imetelstat sodium to the mammal under conditions wherein the hematological malignancy is treated. The mammal can be a human. The method can comprise administering imetelstat sodium to the mammal. The hematological malignancy can be myelofibrosis. The hematological malignancy can be refractory anemia with ringed sideroblasts.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

This document provides methods and materials related to treating hematological malignancies. For example, this document provides methods and materials for using a telomerase inhibitor (e.g., Imetelstat or Imetelstat sodium) to treat a hematological malignancy. As described herein, humans having a hematological malignancy with a spliceosome mutation genotype or presenting with ringed sideroblasts within bone marrow can have an increased likelihood of responding to treatment with a telomerase inhibitor such as Imetelstat or Imetelstat sodium as compared to humans having a hematological malignancy lacking a spliceosome mutation genotype and lacking ringed sideroblasts within bone marrow. In some cases, such humans may have an increased likelihood of experiencing drug toxicity (e.g., myelosuppression) to a greater extent than those humans with a hematological malignancy lacking a spliceosome mutation genotype and lacking ringed sideroblasts within bone marrow. In such cases, those humans can benefit from treatment with a reduced dose, treatment with increased monitoring for toxicity (e.g., increased monitoring for myelosuppression), or both.

In some cases, humans having a hematological malignancy lacking an ASXL1 mutation (e.g., having a wild-type ASXL1 genotype or a germline ASXL1 genotype) can have an increased likelihood of responding to treatment with a telomerase inhibitor such as Imetelstat or Imetelstat sodium as compared to humans having a hematological malignancy with one or more ASXL1 mutations (e.g., an ASXL1 mutation in exon 12 such as a 1934_insG mutation, a 1782C>A mutation, or a 1961-1989_del mutation). In some cases, humans having a hematological malignancy with one or more ASXL1 mutations (e.g., an ASXL1 mutation in exon 12 such as a 1934_insG mutation, a 1782C>A mutation, or a 1961-1989_del mutation) can have a reduced likelihood of responding to treatment with a telomerase inhibitor such as Imetelstat or Imetelstat sodium as compared to humans having a hematological malignancy lacking an ASXL1 mutation (e.g., having a wild-type ASXL1 genotype or a germline ASXL1 genotype).

Any appropriate type of mammal having a hematological malignancy described herein can be treated as described herein. For example, humans, monkeys, dogs, cats, horses, cows, pigs, sheep, mice, and rats having a hematological malignancy with a spliceosome mutation genotype, presenting with ringed sideroblasts within bone marrow, or both can be treated with one or more telomerase inhibitors.

Examples of hematological malignancy that can be treated as described herein. For example, myelofibrosis (e.g., primary myelofibrosis or secondary myelofibrosis), myelofibrosis with a spliceosome mutation genotype, myelofibrosis presenting with ringed sideroblasts within bone marrow, or RARS can be treated using one or more telomerase inhibitors (e.g., Imetelstat or Imetelstat sodium).

Examples of telomerase inhibitors include, without limitation, Imetelstat and Imetelstat sodium. In some cases, one or more than one telomerase inhibitor (e.g., two or three telomerase inhibitors) can be administered to a mammal to treat a hematological malignancy with a spliceosome mutation genotype, presenting with ringed sideroblasts within bone marrow, or both.

Imetelstat sodium is the sodium salt of imetelstat, which is a synthetic lipid-conjugated, 13-mer oligonucleotide N3' P5'-thio-phosphoramidate. The chemical name for Imetelstat sodium is 5'-[O-[2-hydroxy-3-[(1-oxohexadecyl)amino]propyl] phosphorothioate]-d(3'-amino-3'-deoxy-P-thio)(T-A-G-G-G-T-T-A-G-A-C-A-A) (SEQ ID NO:1) sodium salt (13). Imetelstat and Imetelstat sodium can be produced, formulated, or obtained as described elsewhere (Asai et al., *Cancer Res.*, 63(14):3931-3939 (2003), Herbert et al., *Oncogene*, 24:5262-5268 (2005), and Gryaznov, *Chem. Biodivers.*, 7:477-493 (2010)). In some cases, Imetelstat and Imetelstat sodium can be obtained from Geron Corporation (Menlo Park, Calif.).

As described herein, a mammal (e.g., a human) having a hematological malignancy can be assessed to determine if that mammal has a hematological malignancy with the presence of a spliceosome mutation genotype, ringed sideroblasts within bone marrow, or both. Hematological malignancies that contain somatic mutations in SF3B1, U2AF1, or SRSF2 nucleic acid that result in reduced or altered spliceosome activity can be classified as being a hematological malignancy with the presence of a spliceosome mutation genotype. Examples of somatic SF3B1 mutations that can confer a spliceosome mutation genotype include, without limitation, those nucleic acid mutations that result in a K666E amino acid substitution. Additional SF3B1 mutations that can confer a spliceosome mutation genotype include, without limitation, those SF3B1 mutations described elsewhere (Papaemmanuil et al., N. Engl. J. Med. 365:1384-1395 (2011) and Furney et al., Cancer Discov., 3(10):1122-1129 (2013)) such as H662Q and K700E in human SF3B1. Examples of somatic U2AF1 mutations that can confer a spliceosome mutation genotype include, without limitation, those nucleic acid mutations that result in a Q157P amino acid substitution and an 469_insAGTATG mutation. Additional U2AF1 mutations that can confer a spliceosome mutation genotype include, without limitation, those U2AF1 mutations described elsewhere (Graubert et al., Nat. Genet., 44(1):53-57 (2011) and Przychodzen et al., Blood, 122(6):999-1006 (2013)), such as S34Y and S34F in human U2AF1. Examples of somatic SRSF2 mutations that can confer a spliceosome mutation genotype include, without limitation, those SRSF2 mutations described elsewhere (Meggendorfer et al., Blood, 120(15):3080-3088 (2012) and Terra et al., Blood, 120:4168-4171 (2012)), such as P95H, P95L, P95R, P95A, and P95T in human SRSF2.

Examples of ASXL1 mutations that can be used as described herein include, without limitation, ASXL1 mutations present in exon 12 such as a 1934_insG mutation, a 1782C>A mutation, or a 1961-1989_del mutation. Additional ASXL1 mutations that can be used as described herein include, without limitation, those ASXL1 mutations described elsewhere (Thol et al., *J. Clin. Oncol.*, 29(18): 2499-506 (2011)).

Any appropriate method can be performed to detect the presence or absence of a spliceosome mutation genotype. For example, somatic mutations within hematological malignancy cells can be detected using nucleic acid mutation detection techniques such as PCR and nucleic acid sequencing. In some cases, next generation sequences techniques can be used to detect the presence of a spliceosome mutation genotype.

Any appropriate method can be performed to detect the presence or absence of ringed sideroblasts within bone marrow. For example, cell staining and microscopy techniques can be used to detect the presence or absence of ringed sideroblasts within cells obtained from bone marrow biopsies. In some cases, the techniques described elsewhere can be used to detect the presence or absence of ringed sideroblasts within bone marrow (Cazzola and Invernizzi, *Haematologica*, 96(6):789-92 (2011)).

In some cases, a mammal (e.g., a human) identified as having a hematological malignancy with the presence of a spliceosome mutation genotype, ringed sideroblasts within bone marrow, or both as described herein can be treated with one or more telomerase inhibitors (e.g., Imetelstat or Imetelstat sodium). In such cases, when treating with Imetelstat or Imetelstat sodium, the dose of Imetelstat or Imetelstat sodium can be less than 9.4 mg/kg/month. For example, a human identified as having a hematological malignancy with the presence of a spliceosome mutation genotype, ringed sideroblasts within bone marrow, or both can be treated with Imetelstat or Imetelstat sodium at a dose that is between 0.5 mg/kg/month and 9.3 mg/kg/month (e.g., between 1.0 mg/kg/month and 9.3 mg/kg/month, between 2.5 mg/kg/month and 9.3 mg/kg/month, between 5.0 mg/kg/month and 9.3 mg/kg/month, between 6.0 mg/kg/month and 9.3 mg/kg/month, between 0.5 mg/kg/month and 9.0 mg/kg/month, between 0.5 mg/kg/month and 8.0 mg/kg/month, between 6.0 mg/kg/month and 8.0 mg/kg/month, between 6.5 mg/kg/month and 8.0 mg/kg/month, between 7.0 mg/kg/month and 8.0 mg/kg/month, or between 7.2 mg/kg/month and 7.8 mg/kg/month). Telomerase inhibitors such as Imetelstat or Imetelstat sodium can be administered using any appropriate method. For example, telomerase inhibitors such as Imetelstat or Imetelstat sodium can be administered by infusion once a month over a period of time (e.g., one, two, three, four, or five hours).

In some cases, a mammal (e.g., a human) identified as having a hematological malignancy with the presence of a spliceosome mutation genotype, ringed sideroblasts within bone marrow, or both and treated with one or more telomerase inhibitors (e.g., Imetelstat or Imetelstat sodium) at any dose (e.g., 7.5 mg/kg/month or 9.4 mg/kg/month) can be subjected to increased monitoring for drug toxicity. For example, a human presenting with a hematological malignancy having the presence of a spliceosome mutation genotype, ringed sideroblasts within bone marrow, or both who is treated with a telomerase inhibitor such as Imetelstat or Imetelstat sodium can be monitored weekly or every other week for myelosuppression (e.g., decreased or dangerously low platelet and/or white blood cell counts). If significant myelosuppression is detected, then the telomerase inhibitor administration can be ceased or the dose of telomerase inhibitor administered can be reduced (e.g., reduced by 10, 25, 50, or 75 percent).

A composition containing one or more telomerase inhibitors (e.g., Imetelstat or Imetelstat sodium) can be administered to a mammal in any amount, at any frequency, and for any duration effective to achieve a desired outcome (e.g., to reduce a symptom of a hematological malignancy, to increase survival time, to reduce myelofibrosis, and/or to reduce cancer cell proliferation. In some cases, a composition containing one or more telomerase inhibitors (e.g., Imetelstat or Imetelstat sodium) can be administered to a mammal (e.g., a human) having myelofibrosis to reverse bone marrow fibrosis.

Effective doses can vary depending on the severity of the hematological malignancy, the route of administration, the sex, age and general health condition of the subject, excipient usage, the possibility of co-usage with other therapeutic treatments such as use of other agents, and the judgment of the treating physician.

An effective amount of a composition containing one or more telomerase inhibitors (e.g., Imetelstat or Imetelstat sodium) can be any amount that reduces the severity of a symptom of a hematological malignancy (e.g., reduces or reverses bone marrow fibrosis) without producing significant toxicity to the mammal. For example, an effective amount of a telomerase inhibitor such as Imetelstat sodium can be from about 0.5 mg/kg to about 15 mg/kg (e.g., between 1.0 mg/kg and 15 mg/kg, between 5.0 mg/kg and 15 mg/kg, between 0.5 mg/kg and 10 mg/kg, between 5.0 mg/kg and 10 mg/kg, or between 6.0 mg/kg and 8.5 mg/kg). If a particular mammal fails to respond to a particular amount, then the amount can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the hematological malignancy may require an increase or decrease in the actual effective amount administered.

The frequency of administration can be any frequency that reduces the severity of a symptom of a hematological malignancy (e.g., reduces or reverses bone marrow fibrosis) without producing significant toxicity to the mammal. For example, the frequency of administration can be from about once every two months to about once a week, or from about once a month to about twice a month, or from about once every six weeks to about twice a month. The frequency of administration can remain constant or can be variable during the duration of treatment. A course of treatment with a composition containing one or more telomerase inhibitors can include rest periods. For example, a composition containing one or more telomerase inhibitors can be administered weekly over a three week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the hematological malignancy may require an increase or decrease in administration frequency.

An effective duration for administering a composition containing one or more telomerase inhibitors (e.g., Imetelstat or Imetelstat sodium) can be any duration that reduces the severity of a symptom of a hematological malignancy (e.g., reduces or reverses bone marrow fibrosis) without producing significant toxicity to the mammal Thus, the effective duration can vary from one month to several months or years (e.g., one month to two years, one month to one years, three months to two years, three months to ten months, or three months to 18 months). In general, the effective duration for the treatment of a hematological malignancy can range in duration from two months to twenty months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the hematological malignancy.

In certain instances, a course of treatment and the severity of one or more symptoms related to a hematological malignancy can be monitored. Any method can be used to determine whether or not the severity of a symptom of a hematological malignancy is reduced. For example, the severity of a symptom of a hematological malignancy (e.g., bone marrow fibrosis) can be assessed using biopsy techniques.

The invention will be further described in the following examples, which do not limit the scope of the invention described in the claims.

EXAMPLES

Example 1

Inducing Morphologic and Molecular Remissions in Myelofibrosis and Reversing Bone Marrow Fibrosis In an investigator-sponsored single-center study (ClinicalTrials.gov, Identifier: NCT01731951), imetelstat sodium was administered to patients with high or intermediate-2 risk myelofibrosis. Adverse events were monitored by common terminology criteria (Version 4.03), and responses were monitored by the International Working Group criteria. Eligibility criteria included platelets≥50×10$^9$/L.

Imetelstat sodium was administered by a 2-hour intravenous infusion (9.4 mg/kg) every three weeks (cohort A) or weekly×3 followed by every three weeks (cohort B). In addition, patient samples were screened for mutations in ASXL1, SRSF2, SF3B1, and U2AF1 by DNA sequencing. Quantitative PCR was used to measure JAK2V617F burden (assay sensitivity 0.01%). Laboratory correlative studies included analyses of granulocyte telomere length, mononuclear cell telomerase activity, and the presence of human telomerase reverse transcriptase (hTERT) isoforms.

Thirty-three patients were accrued. The first 18 patients who were enrolled and followed for a minimum of three months or discontinued were assessed herein: eleven for cohort A, and seven for cohort B; 44% primary myelofibrosis, 33% post-PV myelofibrosis and 22% post-ET myelofibrosis. The median age was 68 years, and the baseline risk was high in 56% of the patients and intermediate-2 in 44% of the patients. Seven patients were transfusion-dependent. Median spleen size was 13 cm, and eleven patients had constitutional symptoms. Karyotype was abnormal in seven patients, and 89% were JAK2-mutated. Fifteen patients (83%) were previously treated, including seven with a JAK inhibitor and three with pomalidomide.

Toxicity

At a median follow-up of 3.2 months, sixteen patients (89%) remained on treatment. Two patients discontinued treatment because of unrelated death and disease progression. In cohort A, there were no grade-4 treatment-related adverse events. Grade-3 events were limited to thrombocytopenia in 27% of the patients and anemia in 9% of the patients. In cohort B, two patients (29%) experienced grade-4 thrombocytopenia. Grade-3 events were limited to thrombocytopenia, neutropenia, and anemia in one patient each. Dose reduction was necessary in only two patients (11%) because of grade 3 or 4 myelosuppression.

Efficacy

The overall response rate was 44%. This included five patients (28%) who met the bone marrow and peripheral blood morphologic criteria for complete response (CR) (n=4) or partial response (PR) (n=1) and three patients with clinical improvement, pending validation of response duration and resolution of drug-induced grade-1 thrombocytopenia. The four CR patients (22%) experienced reversal of bone marrow fibrosis and recovery of normal megakaryocyte morphology. Two CR patients were transfusion-dependent at baseline and became transfusion-independent. Complete molecular responses were documented in two CR patients. One had U2AF1Q157P and 10% JAK2V617F, and the other had SF3B1K666E and 50% JAK2V617F. A third CR patient had a>50% reduction in U2AF1 469_insAGTATG mutation. Among thirteen patients with leukocytosis, ten patients (77%) normalized their count or had a>50% reduction. Eleven patients (61%) had complete or partial resolution of leukoerythroblastosis.

Mutations

Three patients (50%) of six patients with a spliceosome mutated genotype vs. one patient (8%) of the twelve patients with an unmutated spliceosome genotype achieved CR (p=0.045). Spliceosome-mutated patients also were more likely to experience grade-3/4 myelosuppression (67% vs. 25%; p=0.09). Treatment was associated with suppression of telomerase activity, shortening of telomere length, and alteration of the hTERT isoform pattern.

The likelihood of getting a complete or partial remission from imetelstat among the 33 study patients was 0% among ASXL1-mutated vs. 36% among ASXL1-unmutated cases.

These results demonstrate that telomerase-based treatment strategies such those that involve using imetelstat sodium can be successfully used to treat myelofibrosis. The observed morphologic and molecular remissions confirmed selective anti-clonal activity, which eluded other drugs in myelofibrosis. These results also demonstrate the increased likelihood of successfully treating those patients with a myeloid malignancy having spliceosome mutations.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating myelofibrosis with an increased likelihood of success, wherein said method comprises administering imetelstat or imetelstat sodium to a human identified as having myelofibrosis with the presence of hematological malignancy cells comprising a somatic mutation in SF3B1, U2AF1, or SRSF2 nucleic acid, wherein said myelofibrosis is treated with an increased likelihood of success compared to treating myelofibrosis in a comparable human lacking somatic mutations in SF3B1, U2AF1, and SRSF2 nucleic acid, wherein said somatic mutation in SF3B1 nucleic acid results in an H662Q, K666E, or K700E mutation, wherein said somatic mutation in U2AF1 nucleic acid results in an S34Y, S34F, Q157P, or 469_insAGTATG mutation, and wherein said somatic mutation in SRSF2 nucleic acid results in a P95H, P95L, P95R, P95A, or P95T mutation.

2. The method of claim 1, wherein said method comprises administering imetelstat sodium to said human.

3. A method for treating myelofibrosis with an increased likelihood of success, wherein said method comprises administering imetelstat or imetelstat sodium to a human identified as having myelofibrosis with hematological malignancy cells comprising a germline ASXL1 genotype for said human, wherein said myelofibrosis is treated with an increased likelihood of success compared to treating myelofibrosis in a comparable human having a somatic mutation in ASXL1 nucleic acid.

4. The method of claim 3, wherein said method comprises administering imetelstat sodium to said human.

5. The method of claim 3, wherein said human is a human identified as having myelofibrosis with the presence of hematological malignancy cells comprising a somatic mutation in SF3B1, U2AF1, or SRSF2 nucleic acid, wherein said somatic mutation in SF3B1 nucleic acid results in an H662Q, K666E, or K700E mutation, wherein said somatic mutation in U2AF1 nucleic acid results in an S34Y, S34F, Q157P, or 469 insAGTATG mutation, and wherein said somatic mutation in SRSF2 nucleic acid results in a P95H, P95L, P95R, P95A, or P95T mutation.

6. A method for identifying and treating a human having myelofibrosis with an increased likelihood of success, wherein said method comprises:

(i) detecting the presence of hematological malignancy cells comprising a somatic mutation in SF3B1, U2AF1, or SRSF2 nucleic acid within said human, and (ii) administering imetelstat or imetelstat sodium to said human, wherein said myelofibrosis is treated with an increased likelihood of success compared to treating myelofibrosis in a comparable human lacking somatic mutations in SF3B1, U2AF1, and SRSF2 nucleic acid, wherein said somatic mutation in SF3B1 nucleic acid results in an H662Q, K666E, or K700E mutation, wherein said somatic mutation in U2AF1 nucleic acid results in an S34Y, S34F, Q157P, or 469_insAGTATG mutation, and wherein said somatic mutation in SRSF2 nucleic acid results in a P95H, P95L, P95R, P95A, or P95T mutation.

7. The method of claim 6, wherein said method comprises detecting that said hematological malignancy cells comprise a germline ASXL1 genotype for said human.

* * * * *

SEQUENCE LISTING

<160> NUMBER OF SEQ ID NOS: 1

<210> SEQ ID NO 1
<211> LENGTH: 13
<212> TYPE: DNA
<213> ORGANISM: Artificial Sequence
<220> FEATURE:
<223> OTHER INFORMATION: synthesized 13-mer

<400> SEQUENCE: 1
tagggttaga caa                                                    13